United States Patent [19]

de Bruyne

[11] Patent Number: 4,498,785
[45] Date of Patent: Feb. 12, 1985

[54] FLOATING MAGNETIC STIRRER FOR CULTURE MEDIUM

[75] Inventor: Norman A. de Bruyne, Princeton, N.J.

[73] Assignee: Techne Corporation, Princeton, N.J.

[21] Appl. No.: 432,128

[22] Filed: Sep. 30, 1982

Related U.S. Application Data

[63] Continuation-in-part of Ser. No. 386,764, Jun. 9, 1982, abandoned.

[51] Int. Cl.³ .............................................. B01F 13/08
[52] U.S. Cl. ................................................... 366/274
[58] Field of Search .................... 366/273, 274, 279; 422/224, 225; 435/316, 296

[56] References Cited

U.S. PATENT DOCUMENTS

| | | | |
|---|---|---|---|
| 2,036,076 | 3/1936 | Philippi | 46/239 |
| 2,350,534 | 6/1944 | Rosinger | 366/274 |
| 2,770,073 | 11/1956 | Sullivan | 46/239 |
| 3,172,645 | 3/1965 | Price | 366/273 |
| 3,245,665 | 4/1966 | Steel | 366/273 |
| 4,310,253 | 1/1982 | Sada | 366/273 |

Primary Examiner—Robert W. Jenkins
Attorney, Agent, or Firm—Irvin A. Lavine

[57] ABSTRACT

A stirrer for stirring liquid in a flask comprises a magnetically attractable member formed by or supported by a buoyancy chamber, the stirrer having less density than the liquid to be stirred; the stirrer may include an impeller. A method of stirring a liquid comprising introducing liquid and a buoyant, magnetically attractable stirrer into a vessel, and causing a rotating magnetic field to rotate the stirrer.

32 Claims, 10 Drawing Figures

FLOATING MAGNETIC STIRRER FOR CULTURE MEDIUM

CROSS-REFERENCE TO RELATED APPLICATION

The present application is a continuation-in-part of application Ser. No. 386,764, filed June 9, 1982 by Norman A. de Bruyne, entitled Floating Magnetic Stirrer now abandoned.

TECHNICAL FIELD

The present invention relates to stirrers, and stirring methods, wherein a magnetically attractable stirrer element floats in a body of liquid and is caused to move by a rotating magnetic field.

BACKGROUND ART

Apparatus for stirring liquid materials, including culture mediums, have long been known, particularly stirrer apparatus in which a motor, within a housing, is used to rotate a magnet beneath a platform formed on the housing. On the platfrom, there is a flask having liquid in it, such as liquid culture medium, and a magnet is positioned in the liquid culture medium, and is caused to rotate by the motor-driven magnet in the housing, due to magnetic coupling between the driving magnet and the driven magnet. These magnetic stirrers may generally be classified into two types.

A first type has a cap or top on the flask or other vessel, and the driven magnet is supported by or from this cap or top. Examples of such top-supported driven magnets are as follows. Jacobs, U.S. Pat. No. 2,932,493 discloses a stirrer in which the driven magnet is suspended form the top by a chain or a rod, and is positioned slightly above the bottom of the vessel. Harker, U.S. Pat. No. 3,572,651, provides a flask for stirring a suspension culture of cells in a medium of nutrient substances, includes a magnet supported by a shaft, the shaft being held by a bearing supported by the top or cap of the vessel. Mazowski, U.S. Pat. No. 3,622,129, discloses a construction in which a shaft having a magnet at its lower end extends through or is supported in a bearing in the top or cap. Balas, U.S. Pat. No. 3,854,704, provides a construction in which a stirrer includes a magnet supported by a flexible rod which extends through a stopper of a cell culture container.

A second type of magnetic stirrer apparatus has the driven magnet supported by the bottom of the vessel in which the liquid is contained. Hendricks, U.S. Pat. No. 2,459,224, discloses a stirrer apparatus which includes a magnet at the lower end of a shaft, which rests on the bottom of a container, the shaft having a disc-type agitator fixed to it; rotation of the magnet causes rotation of the shaft and agitator. Steel, U.S. Pat. No. 3,245,665, provides a mixing bar which includes an encapsulating body having a pair of permanent bar magnets embodied in it, and intended to rest on the bottom of a flask and to be rotated by a suitable driven magnet. Bender, U.S. Pat. No. 4,162,855, includes a magnetic rotor mounted within a positioning cage which positions the rotor at the bottom of the vessel; the cage is providedd with bearings for rotatably supporting a magnet.

As an alternative construction to the above-noted provision of a rotating magnet beneath a platform, there has been disclosed an arrangement in which a plurality of static electro-magnets are arranged in a horizontal plane, and circuitry is provided for energizing them in a desired sequence, so as to provide a rotating magnetic field, without actually moving any of the magnets. Such construction is disclosed in Review of Scientific Instruments, March, 1982, pages 369–370, in an article entitled Direct Drive Magnetic Stirrers by chan-Lon Yang and Tzu-Nim Su.

As above noted, it has been recognized that magnetic stirrers are useful in connection with cell culture medium. A survey of the state of this art is found in the article Stirrers for Suspension Cell Cultures by N. A. deBruyne and B. J. Morgan, American Laboratory, June, 1981. That article, among other disclosures, discusses that horizontal rotation of the liquid cell culture medium will not itself cause suspension of particles, but that suspension requires a vertical motion of the liquid. It is also disclosed that where the bearing or support for the shaft is in the top or cap of the vessel or flask, the liquid medium will gradually creep up the rotating vertical shaft and dry out in the bearing. On the other hand, circulation through the bearings, or between a bottom-supported magnet and the bottom, will result in crushing of the particles and microcarriers, if they are used. Microcarriers are tiny solid beads, which are added in large numbers to the nutrient liquid medium, thereby to increase the surface area in the flask, this technique being used in the cultivation of so-called "anchorage dependent cells" which require large areas of solid surface. The noted article also discloses the construction of a flask, known as the Pearson flask, which is characterized by a small conical projection located centrally in the bottom wall of the flask or vessel, which is used in combination with a stirrer suspended from a bearing on the underside of the top or cap of the vessel, on the same axis as the conical projection, the lower end of the stirrer being bulbous and extending into the trough formed between the conical projection and the vertical, cylindrical walls of the flask. The Pearson flask has been found to give the above noted secondary circulation, thereby providing, by definition, vertical motion of the particles, with enhanced culture activity.

Another relevant article is Microcarrier Cell Culture Principles & Methods, published by Pharmacia Fine Chemicals AB, Sweden, 1981. This article discloses a number of rod type stirrers, including the above described Pearson flask with rod stirrer having a bulbous end in the trough.

DISCLOSURE OF INVENTION

The present invention is directed to an apparatus and method in which a stirrer is buoyant relative to the liquid in which it is placed. The stirrer therefore floats in the liquid, and is at the liquid-gas (air) interface. Preferably, the flask is a Pearson flask, having a conical projection located centrally in the bottom, to provide enhanced secondary motion or flow. The buoyant stirrer may be a cylinder of suitable heat-resistant material, sealed at its ends, and containing one or more bar magnets. Alternate constructions include buoyant magnetic stirrers with bulbous end portions either joined together, or held in spaced relation by a connecting linear portion of greater or lesser length, depending upon the size of the flask in which the stirrer is to be placed. In these latter constructions, one or more bar magnets are also placed, extending between two bulbous end portions, and, possibly, into them. In addition, there may be provided a cylinder of magnetic material, having closed ends, and a density less than the density of the liquid medium, so that it will float therein. Preferably, the floating stirrer, in whatever form, has a density approximately one-half of the density of the liquid in which it is placed. The materials, for utility, are able to withstand wet steam of high temperature, such as 123° C.

In addition, the buoyant stirrer may be provided with an impeller positioned to cause or enhance secondary motion or flow of the liquid. The impeller comprises blades, preferably supported beneath the buoyancy chamber and inclined to cause upward movement as the buoyant magnetic stirrer is rotated by the rotating magnetic field.

The herein disclosed method includes the provision of a medium in a flask, and the introduction of a buoyant magnetic stirrer, followed by rotation of the stirrer under the influence of a rotating magnetic field. Preferably, the magnetic field is generated by a magnet below the flask. The floating magnetic stirrer may be used to cause both primary and secondary motion in the liquid, when used in combination with a Pearson flask. In addition, the method contemplates the tilting of the flask, preferably at an angle of approximately 30° to the horizontal, so as to substantially increase the surface area of the liquid, thereby enhancing the contact of the cells with air and enhancing cell growth.

The herein disclosed method also contemplates the introduction into a flask of a buoyant, magnetic stirrer, including an impeller, the flask being either a Pearson flask, or a spherical or substantially spherical flask, preferably.

Among the advantages of the present invention apparatus and method are the elimination of all bearings, ease of cleaning, the elimination of the danger of crushing either cells or microcarriers, the increase of cell proliferation due to secondary motion, creating a suitable stirring action while leaving the liquid free from obstruction as occurs when a magnet is immersed in the liquid, and making full use of the viscous drag on the rotating liquid to generate the above noted secondary motion, thereby harnessing viscous drag to assist in accomplishing the stirring of the liquid with the cells and microcarriers therein. Further, the herein disclosed apparatus has the advantage that any cap or top of the flask is completely free from any encumbrances, such as suspension elements, bearings, etc., and the cap can therefore be removed to provide access to the contents of the flask, so as to permit additions to the contents or withdrawal therefrom, without cessation or interference with the stirring action. Further, in contrast to flasks where there have been provided a cap for suspension or support of the stirrer, there has been necessitated the provision of additional access openings in the flask wall, thereby causing the flask to be somewhat more expensive, the present apparatus having the advantage of eliminating the necessity for such additional access openings in the flask.

MODES FOR CARRYING OUT THE INVENTION

Figure 1:
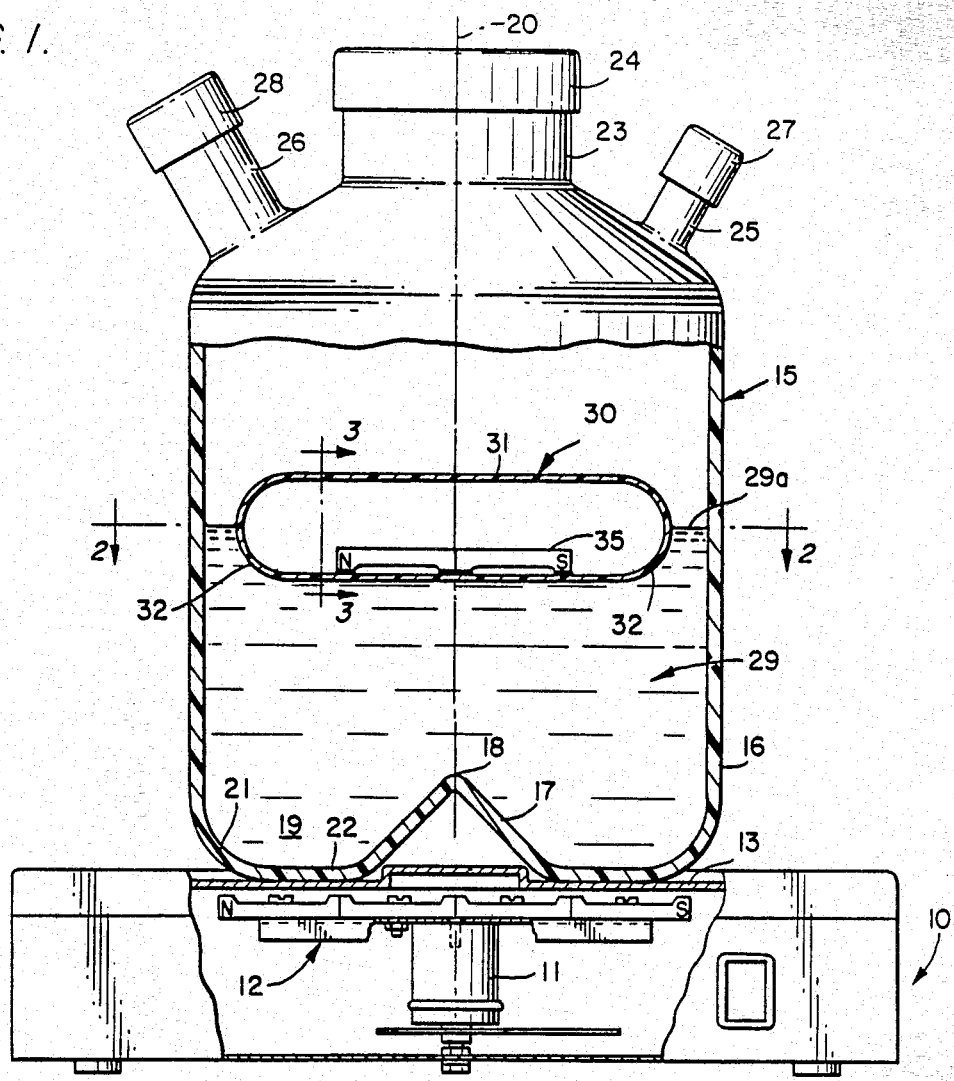
FIG. 1 is an elevational view, partly in section, of a flask having a floating buoyant stirrer in accordance with the invention therein, mounted on a typical magnetic stirrer base.

Referring now to the drawings, wherein like or corresponding reference numerals are used to designate like or corresponding parts throughout the several views, there is shown in FIG. 1 a base housing 10 of conventional construction, and including a motor 11 positioned with its axis vertical, and having connected to the shaft thereof a magnet assembly 12. Magnet assembly 12 will thereby be caused to rotate in a horizontal plane, beneath a seat 13 provided in the upper surface of the base housing 10. Various controls may be provided, as is known in the art, for the actuating and stopping of the motor 11, as well as for controlling its speed of rotation.

On the seat 13 of base housing 10 is a Pearson flask 15 of known construction, including a cylindrical side wall 16, the bottom of Pearson flask 15 having an upstanding conical portion 17 which tapers to a rounded apex 18, thereby forming an interior annular trough or channel 19. The axis of the conical portion 17 lies on the central vertical axis 20 through the flask 15. The bottom corners of the trough or channel 19 are radiused as shown at 21, so as to form a smooth joining of the vertical side walls and the horizontal bottom 22 of Pearson flask 15.

At its upper portion, Pearson flask 15 is provided with a neck 23 having a cap 24 thereon, which may be of plain, unencumbered construction. Access spouts 25 and 26 have caps 27 and 28, respectively, the spouts providing access, if needed, into the interior of the Pearson flask 15, so as to permit additions to or withdrawal of material thereinto. These spouts and caps may be unnecessary, since access may be provided to the interior through the neck 23, without interfering with the stirring operation.

A suitable liquid 29 is contained in Pearson flask 15, having an upper surface 29a exposed to the atmosphere within Pearson flask 15 and perpendicular to axis 20. The liquid 29 may be a cell culture medium, and if it is of the type designated as "anchorage dependent", there may be in the liquid 29 a large number of tiny solid beads, called microcarriers. On the other hand, cultured cells which are "anchorage independent" do not require the utilization of such microcarriers, and the liquid 29 may be of either type of culture cells, included in a suitable nutrient liquid.

A buoyant stirrer 30 is provided in the flask 15, which is preferably of the above noted Pearson flask type. The stirrer 30 comprises a hermetically sealed envelope 31 of generally cylindrical shape having hemispherical ends 32. The envelope 31 is of a material which is non-corrosive, and which will withstand exposure to wet steam at 123° C. Such materials are known in the art, and include Teflon, Tefzel, Kel-F, and Victrex, these being trademarks of various commercially available plastics. The ability to withstand steam of noted temperature insures that the stirrer 30 may be suitably sterilized.

Figure 3:
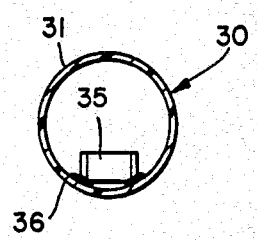
FIG. 3 is a cross-sectional view taken on the line 3—3 of FIG. 1.

Within the envelope 31 is a magnet 35, which is in the form of a bar, and may be made up of a plurality of bar magnets placed end to end. As shown in FIG. 3, a suitable adhesive 36 may be utilized to secure the magnet 35 to the interior wall of the envelope 31.

The volume of the hermetically sealed envelope 31 is greater than the volume of bar magnet 35, the remaining space in envelope 31 being occupied by air or other gas to cause stirrer 30 to be buoyant. The density of the stirrer 30 is less than the density of the liquid 29, and is preferably approximately one half of the density of the liquid 29 so that the stirrer is about half-submerged, as shown.

Figure 2:
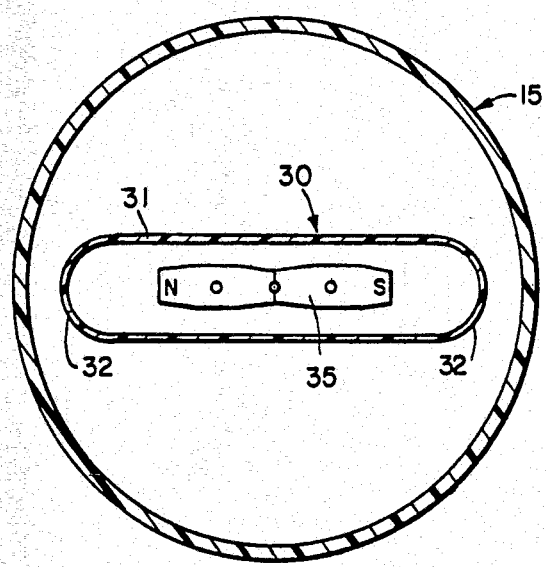
FIG. 2 is a cross-sectional view taken on the line 2—2 of FIG. 1.

As shown in FIG. 2, the bar magnet 35, housed within the envelope 31, has its axis generally parallel to the axis of the cylindrical portion of the envelope 31. The length of the stirrer 31 is as shown greater than the radius and less than the diameter of the Pearson (or other) flask 15.

Upon actuation of the motor 11, the magnetic field from the magnet assembly 12 will cause the stirrer 30 to rotate, generally on the axis 20 of the flask 15 which extends therethrough, due to magnetic coupling between the magnets of the magnet assembly 12 and the magnet(s) 35. The magnetic field will prevent the stirrer 30 from engaging the walls of the Pearson or other flask 15, thereby avoiding crushing of the cells. In addition, it is possible that hydrodynamic forces will tend to keep the stirrer 30 centered in the Pearson or other flask 15, avoiding crushing of cells between the stirrer 30 and the walls 16 of flask 15. The stirring action of stirrer 30 on the liquid 29 will serve to keep all of the cells, and microcarriers, if present, in suspension, due to both the primary flow and the secondary flow or motion generated by the construction of the Pearson flask 15. With the present invention construction, and method, the buoyant stirrer 30, located at the top layers of the liquid 29, leaves the bulk of the liquid 29 free of all obstructions, thereby making full use of the viscous drag on the rotating liquid. This also assists in generating the above noted secondary motion which provides for the suspension of the cells and microcarriers, if present. Thus, with the disclosed apparatus and concomitant method, viscous drag is harnessed to stir and keep the cells and microcarriers, if present, in suspension.

Figure 4:
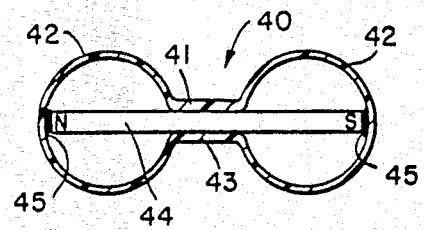
FIG. 4 is a cross-sectional view of an alternate embodiment of a buoyant, floating stirrer in accordance with the present invention.

In FIG. 4, there is shown an alternate embodiment in which the stirrer 40 comprises an envelope 41 having bulbous elements 42 at the ends thereof, and connected by a linear portion 43 of generally cylindrical configuration. The bulbous elements are, of course, hollow and the envelope 41, as are all of the envelopes herein disclosed, is hermetically sealed. The linear portion 43 may be of greater or lesser extent, providing a stirrer 40 of greater or lesser length. Within the envelope 41 is a bar magnet 44, secured by suitable adhesive 45. The bar magnet 44 is seen extending between the polar regions of the two bulbous elements 42, but may be of lesser length, in which case the bar magnet 44 may be adhered to other portions of the envelope 41.

Figure 5:
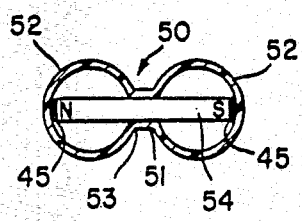
FIG. 5 is a view similiar to FIG. 4, showing another embodiment of a floating magnetic stirrer.

In FIG. 5 there is shown another embodiment of a stirrer designated 50, and having an envelope 51 with a pair of bulbous elements 52. A very short linear portion 53 extends between the bulbous elements 52. A bar magnet 54 is provided, extending (similar to the construction in FIG. 4) through the linear portion 53 and through the bulbous elements 52, being joined by adhesive 45 to the polar regions of the bulbous elements 52.

Figure 6:
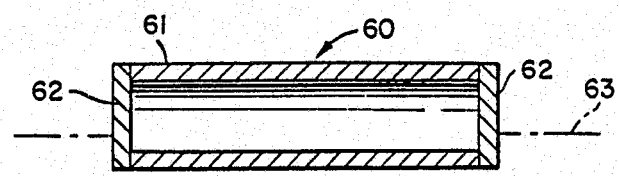
FIG. 6 is a view similiar to FIG. 4, showing still another embodiment of a floating magnetic stirrer in accordance with the present invention.

In FIG. 6, there is shown still another embodiment of a stirrer in accordance with the present invention, there being disclosed therein a stirrer 60 comprising a cylindrical, hollow body 61 of magnetically attractable material. To seal the elongate, hollow cylindrical body 61, there are provided end caps 62 of any suitable material, secured or adhered to the ends of the body 61, so as to provide a hermetically sealed construction. The body 61, being of magnetically attractable material, will be caused to rotate in the same manner as the stirrers hereinabove disclosed. The stirrer 60, like the other stirrers, has a density less than the density of the liquid medium in which it is to be used, and so will float therein, as indicated by the line 63, which indicates the liquid surface. As will be understood, the body 61 is preferably a hollow magnet.

Figure 7:
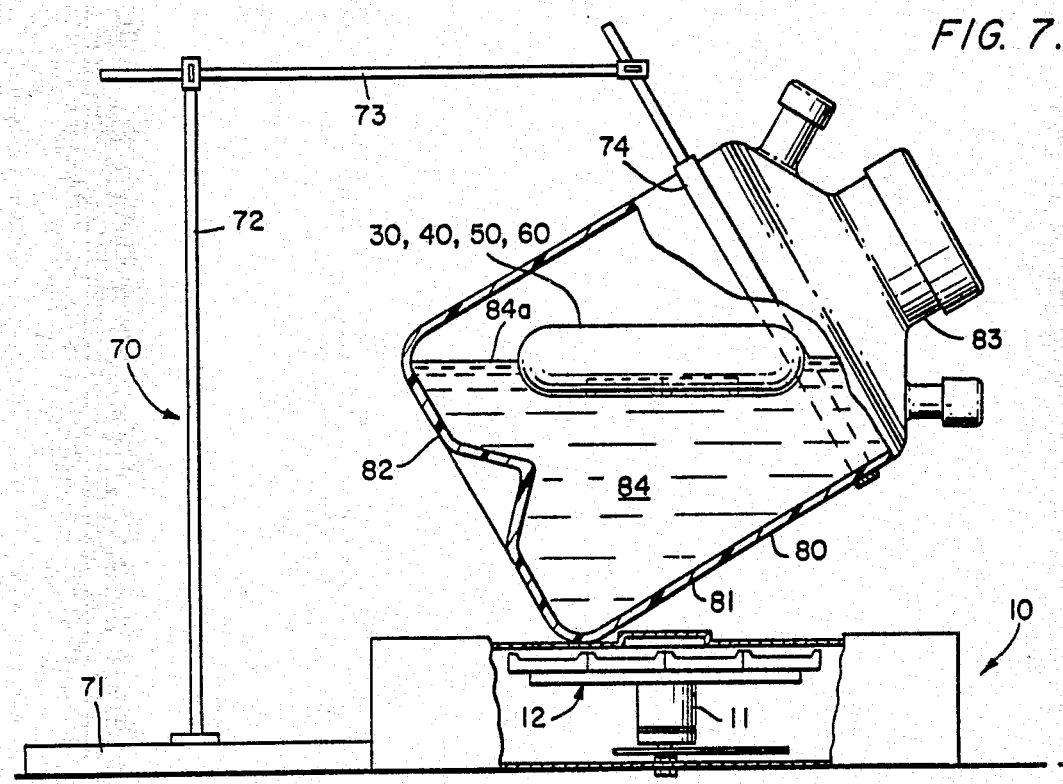
FIG. 7 is an elevational view disclosing a magnetic stirrer in a flask in an inclined position, in accordance with the present invention.

Referring now to FIG. 7, there is disclosed a base housing 10 with motor 11 having its axis vertical, and having a magnet assembly 12 connected to and driven by the shaft of motor 11. A support 70 is provided for a vessel 80. The support 70 may be a typical chemical laboratory stand, including a base 71, trunk 72, horizontal arm 73 and clamp 74 of known construction, for engaging and supporting the vessel 80. The vessel 80 is of conventional construction, having cylindrical walls 81, and a bottom 82 perpendicular thereto, and with a neck 83 at its upper end, opposite the bottom 82. The clamp 74 and the support 70 serve to position and hold the vessel 80 with its axis at an angle of 30° to the horizontal. Within the vessel 80 is a suitable liquid 84 having a surface 84a. The area of surface 84a, when the vessel 80 is inclined as above noted, has an area approximately double the area of the surface when the vessel 80 is upright, with its axis vertical.

A buoyant, magnetic stirrer 30, 40, 50, 60 is contained within the vessel 80 and floats half-submerged in the upper region of the liquid 84. It is rotated in the manner hereinabove described on an axis extending through it, perpendicular to surface 84a by the magnetic field of the magnet assembly 12, and will be maintained in position away from the wall 81 of vessel 80 so as to avoid crushing cells and microcarriers. The enhanced surface area 84a of the liquid 84 facilitates gas absorption and allows more cells to come to the surface in a given time. This enhances the growth of the cells, accelerating cell production.

Figure 8:
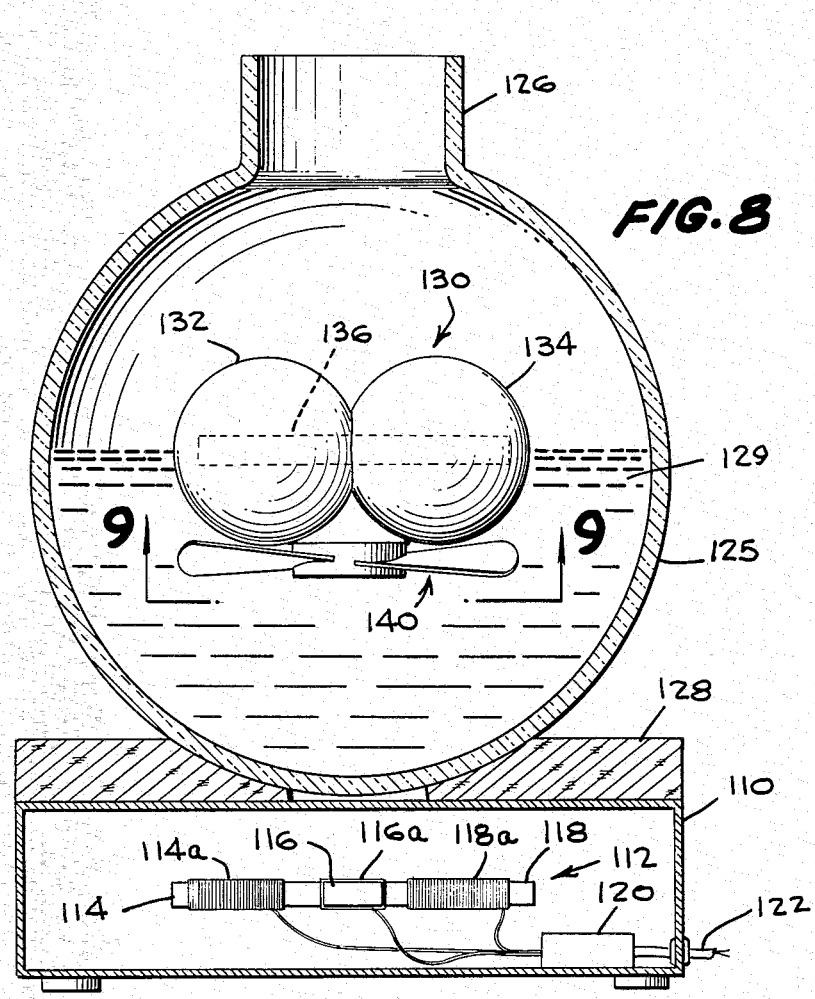
FIG. 8 is a cross-sectional view, with parts in elevation, of alternate stirrer apparatus, including a stirrer having an impeller.

In FIG. 8, there is disclosed a base housing 110 having therein a rotating magnetic field generator 112, which includes a plurality of coil windings 114, 116 and 118, there being, a fourth coil winding not shown in FIG. 8. These four coil windings are connected magnetically to form two electromagnets at right angles to each other and the coils are connected to suitable circuit means 120, connected by conductor 122 to a suitable source of electricity in known manner. The rotating magnetic field generator 112 is preferably made as provided in the article Direct Drive Magnetic Stirrers hereinabove referenced.

A generally spherical flask 125 is shown, having a neck opening 126; the flask 125 preferably has a rounded bottom, but, optionally, a portion of the bottom may be flattened. As shown, the flask 125 has a round bottom, and is supported in a cork ring 128.

Within the flask 125 is a floating stirrer 130 which may comprise hollow, generally spherical elements 132 and 134. These may be made of a suitable plastic material, such as polypropylene. A suitable hole will have been made in each of the elements 132 and 134, and a bar magnet 136 inserted into the elements 132 and 134, and then the elements are secured together, in a hermetic fashion, thereby encasing the bar magnet 136 in a hermetically sealed, buoyant envelope. The elements 132 and 134 may be more or less flattened at their abutting surface portions.

Figure 9:
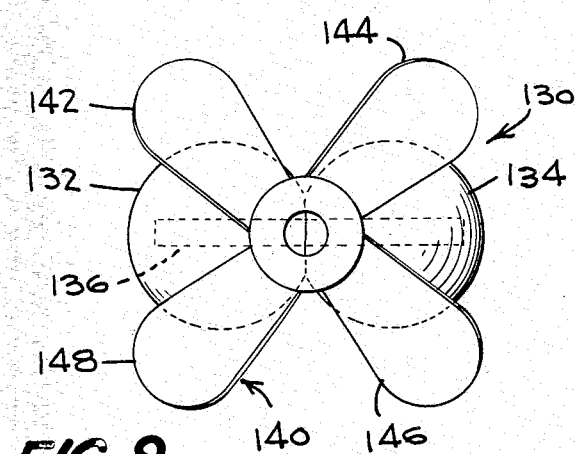
FIG. 9 is a view taken on the line 9—9 of FIG. 8.

The buoyant magnetic stirrer 130 comprises, additionally, an impeller 140, for causing upward movement or secondary motion of liquid 129 within flask 124, in which the buoyant magnetic stirrer 130 floats. The impeller 140 has, as shown in FIG. 9, four blades 142, 144, 146 and 148, although a greater or lesser number of blades may be utilized. The blades 142-148 have a radial extent approximately equal to the length of the assemblage of the elements 132 and 134, and as will be understood, the entire stirrer 130 has dimensions so related to the neck opening 126 that it may pass therethrough. Thus, the drawings will be understood to be generally descriptive, rather than dimensional.

Figure 10:
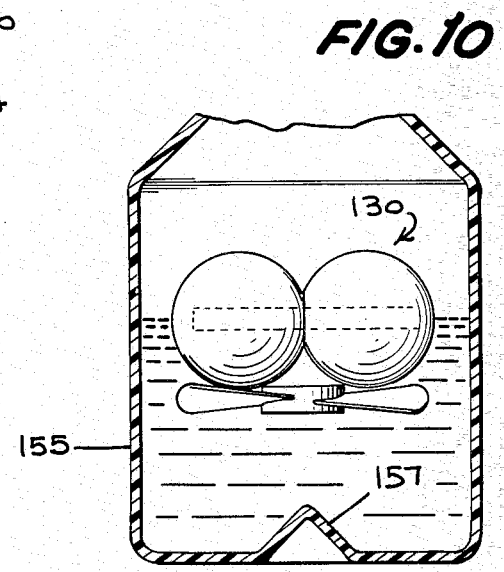
FIG. 10 is a cross-sectional view, with parts broken away and in elevation, of a buoyant magnetic stirrer with impeller, in a Pearson flask.

In FIG. 10, there is provided a Pearson flask 155, generally of the type disclosed in FIG. 1, and the floating magnetic stirrer with impeller 130 is provided therein. The Pearson flask will be seen to have an upstanding conical portion 157, similiar to the portion 17, and otherwise generally be the same as and function in the same manner as the Pearson flask shown in FIG. 1.

In operation, the buoyant magnetic stirrer with impeller provides for superior performance, because if the enhancement of the secondary motion which is imparted to the culture medium, upon rotation of the stirrer under the impetus of the rotating magnetic field.

There has been provided an apparatus for stirring liquid, particularly cell culture medium, which includes a buoyant magnetic stirrer. The buoyant magnetic stirrer may have different embodiments, including a plastic envelope housing one or more bar magnets, the envelope being cylindrical, with hemispherical end portions, or having bulbous elements at the ends, with a linear connecting portion. The buoyant magnetic stirrer may be provided with an impeller, to provide an enhanced secondary motion of the culture medium. In addition, the stirrer may be a cylindrical magnet, hollow and with end closures to provide buoyancy, all of the stirrers being of lesser density than the liquid, preferably having a density of approximately one-half of that of the liquid. The herein disclosed buoyant magnetic stirrer may be utilized with a conventional flask, or with a Pearson flask, characterized by a conical projection at the bottom, forming an annular trough or channel in the bottom of the flask. In addition, the present invention contemplates a method of stirring, using a buoyant stirrer, within a vessel having its axis either vertical, or tilted, preferably at 30° to the horizontal.

The herein disclosed apparatus and method avoid either submerged bearings or bearings in a cap, thereby avoiding both the damaging of cells and microcarriers, if present, and avoiding a cap with encumberances, making it difficult to clean. The herein disclosed carrier is made of material enabling it to withstand sterilization by high temperature wet steam, and there may be enhanced, by the present invention stirrer apparatus and method, the secondary flow or motion and thereby enhancement of the suspension action of the cells in the medium. Where the axis of the vessel is tilted, enhanced exposure of the cells to atmosphere results.

It will be obvious to those skilled in the art that various changes may be made without departing from the spirit of the invention, and therefore the invention is not limited to that shown in the drawings and described in the specification, but only as indicated in the appended claims.

I claim:

1. A stirrer apparatus for stirring a liquid medium in a flask comprising:
   (a) a flask for holding liquid medium,
   (b) stirrer means for stirring substantially all of the liquid medium in the flask comprising an element of magnetically attractable material, and buoyant means for supporting said element in the liquid medium in the flask, said element and said buoyant means having a density less than the density of the liquid medium, and
   (c) means for causing said stirrer means to rotate while supported in the liquid medium generally about an axis substantially perpendicular to the surface of the liquid medium, said axis extending through said stirrer means,
   whereby the stirrer means is rotated by said rotating magnetic field and effects the stirring of substantially all of the liquid medium in the flask.

2. The stirrer apparatus of claim 1, said element comprising a bar magnet.

3. The stirrer apparatus of claim 1, said buoyant means comprising an envelope housing said element.

4. The stirrer apparatus of claim 2, said buoyant means comprising a hermetically sealed envelope, said bar magnet being within said envelope.

5. The stirrer apparatus of claim 4, said envelope comprising a cylinder, said bar magnet being substantially parallel to the envelope axis.

6. The stirrer apparatus of claim 5, said cylinder having hemispherical ends.

7. The stirrer apparatus of claim 5, said envelope having a pair of bulbous elements at the ends thereof.

8. The stirrer apparatus of claim 4, said envelope comprising a pair of spherical elements.

9. The stirrer apparatus of claim 1, the stirrer means having a density approximately one-half of the density of the liquid.

10. The combination of claim 1, said flask having cylindrical walls, a bottom, and means defining a trough in the bottom part of the flask comprising a centrally located upstanding conical portion.

11. The stirrer apparatus of claim 1, said rotating field creating means comprising a magnet, and means for rotating said magnet.

12. The combination of claim 11, said flask being above said last mentioned magnet.

13. The combination of claim 11, said flask having a longitudinal axis, and means for supporting said flask with its axis inclined to the vertical.

14. The stirrer apparatus of claim 1, and said stirrer means further comprising impeller means for generating an upward flow of liquid medium in said flask.

15. The stirrer of claim 14, the stirrer means having a density less than that of said liquid.

16. The combination of claim 15, said impeller means comprising blades in said liquid beneath said buoyant means.

17. A stirrer for use in stirring a liquid medium in a vessel comprising:
   (a) a linearly extending body of magnetically attractable material,
   (b) a hermetically sealed, buoyant envelope encompassing said body being of greater volume than said body, and being of plastic material capable of withstanding wet steam at 123°,
   (c) said magnetically attractable body and said buoyant envelope together having a density less than the density of the liquid medium.

18. The stirrer of claim 17, said envelope having bulbous ends.

19. The stirrer of claim 17 or 18, said stirrer comprising impeller means for generating an upward flow of liquid medium in a flask in which said stirrer is placed.

20. The stirrer of claim 17, said magnetically attractable body being a bar magnet.

21. A method of stirring a liquid medium comprising placing said medium in a flask, stirring substantially all of the liquid in said flask by placing the flask with the liquid therein in a rotating magnetic field and placing in said flask a magnetic stirrer buoyant relative to said liquid and capable of causing the stirring of substantially all of the liquid in the flask when rotated, and causing said rotated magnetic field to rotate said stirrer about an axis extending therethrough and which axis is substantially perpendicular to the surface of the liquid.

22. The method of claim 21, wherein the flask has an upstanding conical portion centrally located in the bottom thereof to define a trough thereabout with the side walls of the flask, said side walls being equally distant from the axis of said conical portion, and positioning said flask with the axis of said conical portion substantially perpendicular to the plane of rotation of said buoyant magnetic stirrer.

23. The method according to claim 22, further comprising inclining the flask to the horizontal, and rpotating the buoyant magnetic stirrer in a substantially horizontal plane while the flask is inclined.

24. The method of claim 23, wherein the placing of said medium is of an amount to partially fill the flask so as to leave a substantial space above the liquid level with the flask in the tilted position.

25. The method of claim 24, wherein the step of placing liquid medium in the flask comprises the step of placing cell culture medium in the flask.

26. The method of claim 21 or 22, further comprising placing in said flask a buoyant member comprising an impeller for causing upward flow of liquid medium.

27. The method of claim 21, further comprising providing a spherical flask, and placing in said flask a buoyant member comprising an impeller causing an upward flow of the liquid.

28. A stirrer apparatus for stirring a liquid medium in a flask comprising:
   (a) a flask for holding liquid medium having an opening at the top and being generally symmetrical about an axis extending through said opening,
   (b) stirrer means for stirring substantially all of the liquid medium in the flask comprising an element of magnetically attractable material, buoyant means for supporting said element in the liquid medium in the flask, said element and said buoyant means having a density less than the density of the liquid medium, said stirrer having a length greater than the radius and less than the diameter of the flask at the surface of liquid culture medium therein; and
   (c) magnetic field means for causing said stirrer means to rotate while supported in the liquid medium generally about an axis passing therethrough, said last mentioned axis being substantially perpendicular to the surface of the liquid medium and substantially at the center of said liquid medium surface.

29. The stirrer apparatus of claim 28, said stirrer means being approximately half-submerged in said liquid medium.

30. The stirrer apparatus of claim 29, said stirrer means further comprising impeller means for generating an upward flow of liquid medium in said flask.

31. The stirrer apparatus of claim 28, said stirrer means further comprising impeller means for generating an upward flow of liquid medium in said flask.

32. The stirrer apparatus of claim 28 said flask having cylindrical walls, and means defining a trough in the bottom part of the flask comprising a centrally located upstanding conical portion.

* * * * *